US007947626B2

(12) United States Patent
Ma et al.

(10) Patent No.: US 7,947,626 B2
(45) Date of Patent: May 24, 2011

(54) PASSAGED NEURAL STEM CELL-DERIVED NEURONAL NETWORKS AS SENSING ELEMENTS FOR DETECTION OF ENVIRONMENTAL THREATS

(75) Inventors: Wu Ma, Silver Spring, MD (US); Jinny Lin Liu, Ellicott, MD (US); Thomas O'Shaughnessy, College Park, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 758 days.

(21) Appl. No.: 11/846,810

(22) Filed: Aug. 29, 2007

(65) Prior Publication Data

US 2008/0058223 A1    Mar. 6, 2008

Related U.S. Application Data

(60) Provisional application No. 60/824,167, filed on Aug. 31, 2006.

(51) Int. Cl.
| | |
|---|---|
| C40B 50/06 | (2006.01) |
| C40B 60/04 | (2006.01) |
| C12N 5/00 | (2006.01) |
| C12N 5/079 | (2006.01) |
| A01N 63/00 | (2006.01) |

(52) U.S. Cl. ............ 506/26; 506/35; 435/325; 435/378; 435/395; 424/93.7

(58) Field of Classification Search .................... 506/26, 506/35; 435/325, 378, 395; 424/93.7
See application file for complete search history.

(56) References Cited

U.S. PATENT DOCUMENTS

| 5,851,832 | A * | 12/1998 | Weiss et al. .................... 435/368 |
| 6,197,575 | B1 | 3/2001 | Griffith |
| 6,654,729 | B1 * | 11/2003 | Hickman et al. ................ 706/15 |
| 2003/0054333 | A1 * | 3/2003 | Hickman et al. ................. 435/4 |
| 2004/0106168 | A1 | 6/2004 | Evans |

OTHER PUBLICATIONS

Tomaselli et al., 1986, Distinct Molecular Interactions Mediate Neuronal Process Outgrowth on Non-neuronal Cell Surfaces and Extracellular Matrices, The Journal of Cell Biology, 103(6, pt. 2): 2659-2672.*
O'Shaughnessy et al., 2009, Passaged neural stem cell-derived neuronal metworks for a portable biosensor, Biosensors and Bioelectronics, 24: 2365-2370.*
Ma et al., 1998, Basic FGF-Responsive Telencephalic Precursor Cells Express Functional GABA Receptor/CI Channels in vitro, J. Neurobiol., 35: 277-286.*

Long et al., Neural Cell Differentiation in vitro from Adult Human Bone Marrow Mesenchymal Stem Cells, Stem Cells and Development, 14: 65-69.*
Park et al., 2004, Generation of dopaminergic neurons in vitro from human embryonic stem cells treated with neurotrophic factors, Neuroscience Letters, 359: 99-103.*
Gray, S.A., et al. "Design and demonstration of an automated cell-based biosensor," Biosens. Bioelectron. 16, 535-542, 2001.
Gross, G.W., et al. "Odor, Drug, and Toxin Analysis with Neuronal Networks in Vitro: Extracellular Array Recording of Network Responses," Biosens. Bioelectron. 12, 373, 1997.
Gross, G.W., et al. "Stimulation of monolayer networks in culture through thin-film indium-tin oxide recording electrodes," J. Neuroscience Methods. 50, 131-143, 1993.
Hosomi, S., et al. "The p75 receptor is required for BDNF-induced differentiation of neural precursor cells," Biochem. Biophys. Res. Commun. 301,1011-5, 2003.
Kulagina, N., et al. "Detection of Marine Toxins, Brevetoxin-3 and Saxitoxin, in Seawater Using Neuronal Networks," Environ. Sci. Technol. 40, 578-583, 2006.
Kulagina, N., et al. "Pharmacological effects of the marine toxins, brevetoxin and saxitoxin, on murine frontal cortex neuronal networks," Toxicon. 44, 669-676, 2004.
Liu, Q.Y., et al. "Astrocyte-conditioned saline supports embryonic rat hippocampal neuron differentiation in short-term cultures," J. Neuroscience Methods. 86, 71-7, 1998.
Ma, W., et al. "Basic FGF-responsive telencephalic precursor cells express functional GABAA receptor/CI- channels in vitro," J. Neurobiol., 35, 277-286, 1998.
Mistry, S.K.. et al. "Cultured rat hippocampal neural progenitors generate spontaneously active neural networks," P.N.A.S., 99,1621-1626, 2002.
O'Shaughnessy, T.J. et al. "Cultured neuronal networks as environmental biosensors." J. Appl. Toxicol. 24, 379-385, 2004.
Panchision, D.M., et al. "The control of neural stem cells by morphogenic signals," Curr. Opin. Genet. Dev. 12, 478-87, 2002.
Pancrazio, J.J., et al. "A Portable Microelectrode Array Recording System Incorporating Cultured Neuronal Networks for Neurotoxin Detection," Biosens. Bioelectron. 18, 1339, 2003.
Pancrazio, J.J., et al. "Development and Application of Cell-Based Biosensors," Biomedical Engineering Society. 27, 697-722, 1999.
Shaffer, K.M., et al. "The use of GABAA receptors expressed in neural precursor cells for cell-based assays," Biosen. Bioelectron. 16, 481-489, 2001.
Shaffer, K.M., et al. "Neuronal Network Biosensor for Environmental Threat Detection," 2004 NRL Review. 118-120, 2004.

(Continued)

*Primary Examiner* — Amber D. Steele
(74) *Attorney, Agent, or Firm* — Amy Ressing; Roy Roberts (57) ABSTRACT

This invention comprises a method for generating functional neural networks using neural progenitor cells on microelectrode arrays (MEAs). The method involves dissociating neural progenitor cells from an embryo, propagating the neural progenitor cells, passaging the neural progenitor cells and seeding the neural progenitor cells on MEAs to produce a functional neural network. The neural progenitor cells may be continuously passaged to propagate an endless supply of neural progenitor cells. The resultant passaged progenitor cell derived neural network MEA may be used to detect and/or quantify various biological or chemical toxins.

16 Claims, 5 Drawing Sheets

OTHER PUBLICATIONS

Stenger, D.A., et al. "Detection of physiologically active compounds using ell-based biosensors," Trends in Biotech. vol. 19, No. 8, 304-309, 2001.

Zheng, W., et al. "Fibroblast growth factor 2 is required for maintaining the neural stem cell pool in the mouse brain subventricular zone," Dev. Neurosci. 26, 181-96, 2004.

* cited by examiner

PASSAGED NEURAL STEM CELL-DERIVED NEURONAL NETWORKS AS SENSING ELEMENTS FOR DETECTION OF ENVIRONMENTAL THREATS

CROSS-REFERENCE TO RELATED APPLICATIONS

This Application is a Non-Prov of Prov (35 USC 119(e)) application 60/824,167 filed on Aug. 31, 2006, incorporated herein by reference in its entirety.

BACKGROUND OF THE INVENTION

This invention relates to a method for making neural network microelectrode arrays derived from passaged progenitor cells. The array may be used for various biosensing applications including detection and/or quantification of various biological, chemical or environmental threats, including toxins, such as neurotoxins, nerve agents, such as neurotransmitter antagonists and neurotransmitter inhibitors, bacterial agents, viral agents, choking agents, fuel and/or combustion products, toxic metals, herbicides and/or pesticides, bioregulators, psychogenic and/or hallucinatory drugs, n-acyl ethanolamines and other miscellaneous compounds.

Traditional biosensor technologies operate by detecting specific, known environmental threats. Recent technological advances have led to the development of more broad-spectrum generic detection methodologies to complement target specific sensors and assays. These generic biosensors utilize the functional responses of a biological system as sensor elements to detect and/or quantify both known and unknown toxins.

For example, neural network microelectrode arrays derived from primary neural tissue have been shown to detect a range of environmental toxins in various media such as samples of potable water and sea water. (Shaffer, K. M., Gray, S. A., Fertig, S. G., Selinger, J. V., O'Shaughnessy, T. J., Kulagina, N. V., Stenger, D. A., and Pancrazio, J. J., "Neuronal Network Biosensor for Environmental Threat Detection," 2004 NRL Review, chemical/biochemical research, pp. 118-120, (2004); Kulagina, N., et al. "Pharmacological effects of the marine toxins, brevetoxin and saxitoxin, on murine frontal cortex neuronal networks," Toxicon 44, pp. 669-676, (2004); Kulagina, N., et al. "Detection of Marine Toxins, Brevetoxin-3 and Saxitoxin, in Seawater Using Neuronal Networks," Environ. Sci. Technol. 40, pp. 578-583, (2006); O'Shaughnessy, T. J., Gray, S. A., Pancrazio, J. J., "Cultured neuronal networks as environmental biosensors," J. Appl. Toxicol. 24, pp. 379-385, (2004)). These arrays utilize networks of mammalian neurons as sensing elements. The networks are grown over thin-film microelectrode arrays (MEAs), which enable extracellular monitoring of bioelectrical activity over at least 64 MEA contact points (Gross, G. W., Harsch, A., Rhoades, B K., Gopel, W., "Odor, Drug, and Toxin Analysis with Neuronal Networks in Vitro: Extracellular Array Recording of Network Responses." Biosens. Bioelectron. 12, 373, (1997): Pancrazio, J. J., Gray, S. A., Shubin, Y. S., Kulagina, N., Cuttino, D. S., Shaffer, K. S., Eisemann, K., Curran, A., Zim, B., Gross, G. W., and O'Shaughnessy, T. J., "A Portable Microelectrode Array Recording System Incorporating Cultured Neuronal Networks for Neurotoxin Detection." Biosens. Bioelectron. 18, p. 1339, (2003)). Changes in action potential dynamics across the neural network. i.e. the rate at which action potentials are fired across the neural network, can be used as a basis for detecting neuron-active substances (Pancrazio, J. J., et al., "Development and Application of Cell-Based Biosensors." Biomedical Engineering Society 27, pp. 697-722. (1999): Stenger, D. A., et al., "Detection of physiologically active compounds using cell-based biosensors." Trends in Biotech, Vol. 19, no. 8, pp. 304-309, (2001)).

The action potentials observed in the networks are largely driven by the synaptic integrity of the network, rather than being the result of independent spiking neurons. Thus, compounds that affect the synapses dramatically affect the overall rate at which action potentials are fired across the network. Extracellular monitoring of bioelectrical activity from cultured networks grown over MEAs is a noninvasive method that enables long-term monitoring. The neural network MEA derived from primary neural tissue can potentially be configured as a portable instrument that requires only minimal training to operate (Pancrazio, J. J., Gray, S. A., Shubin, Y. S., Kulagina, N., Cuttino, D. S., Shaffer, K. S., Eisemann, K., Curran, A., Zim, B., Gross, G. W., and O'Shaughnessy, T. J., "A Portable Microelectrode Array Recording System Incorporating Cultured Neuronal Networks for Neurotoxin Detection." Biosens. Bioelectron. 18, p. 1339, (2003)).

The primary neural tissue cultures used to generate these neural networks, however, are difficult to obtain and require the use of a significant number of animals in order to provide sufficient source material for the tissue cultures. Recently, scientists have been experimenting with stem cells and progenitor cells as an alternative, self-renewing resource capable of forming neural networks. Whereas primary cultures of neural stem cells and progenitor cells, which are isolated directly from developing animal brains, provide a limited amount of neural tissue, a single progenitor cell culture, which may be induced to form functional neural networks, can potentially regenerate for an indefinite period of time through cell passaging. Passaging cells may involve splitting cells by protease treatment and detaching the cells from the culture surface before the cell density becomes confluent. Trypsin is commonly used for detachment and such a splitting process can be repeated multiple times, however, eventually the cells stop proliferating due to other stresses. (Shaffer, K. M., Lin, H. J., Maric, D., Pancrazio, J., Stenger, D. A., Barker, J. L., Ma, W., "The use of $GABA_A$ receptors expressed in neural precursor cells for cell-based assays." Biosensors & Bioelectronics, 16, pp. 481-489, (2001)).

U.S. Pat. No. 6,197,575 discloses a matrix seeded with undifferentiated cells, such as embryonic cells, stem cells and other precursor cells. The matrix may be used to detect biological toxins. U.S. Patent Publication no. 2004/0106168 also discloses a neural network grown on an MEA from primary neural tissue cultures. This document also suggests that 12-16 day old embryonic cells may be plated on the MEA to generate the neural network but does not exemplify such a method. Mitogenic growth factors can synergize with N-CAM or neurotrophins to generate spontaneously active neural networks on MEAs from neural progenitor cells. Mistry, S. K., Keefer, E. W., Cunningham, B. A., Edelman, G. M., Crossin, K. L., "Cultured rat hippocampal neural progenitors generate spontaneously active neural networks," PNAS. 99, pp. 1621-1626, (2002). This method for generating neural networks from neural progenitor cells, which consists of disassociating embryonic stem cells from the hippocampal region, growing the cells in a serum free medium and plating the disassociated cells, is inefficient and produces a limited amount of neuroglia and neurons. Mistry, S. K., Keefer, E. W., Cunningham, B. A., Edelman, G. M., Crossin, K. L., "Cultured rat hippocampal neural progenitors generate spontaneously active neural networks." PNAS. 99, pp. 1621-1626, (2002).

Although neural stem cells and progenitor cells are capable of self-renewal and differentiating into functional neural networks and, as such, can be utilized to mass produce cells for biosensor or pharmacologic testing, the natural differentiation process is complex and far from fully understood. Several approaches have been used to induce neural stem cell differentiation into functional neural networks. The majority of these methods focus on providing various culture conditions and means for regulating differentiation. Growth factors, neurotrophins and cell adhesion molecules have been shown to regulate neural stem cell differentiation (Panchision, D. M., McKay, R. D., "The control of neural stem cells by morphogenic signals." *Current Opinion Genetic Dev.* 12, pp. 478-87, (2002): Hosomi S, Yamashita T, Aoki M, Tohyama M., "The p75 receptor is required for BDNF-induced differentiation of neural precursor cells." *Biochem Biophys Res Commun.* 301, pp. 1011-5, (2003): and Zheng, W., Nowakowski, R. S., Vaccarino, F. M., "Fibroblast growth factor 2 is required for maintaining the neural stem cell pool in the mouse brain subventricular zone." *Dev Neurosci.* 26, pp. 181-96, (2004)). Basic fibroblast growth factor (bFGF) is a growth factor that has been demonstrated to promote cell proliferation and neurogenesis (Ma, W., Liu, Q. Y., Maric, D., Sathanoori, R., Chang, Y. and Barker, J. L. "Basic FGF-responsive telencephalic precursor cells express functional $GABA_A$ receptor/$Cl^-$ channels in vitro," *J. Neurobiol,* 35, pp. 277-286 (1998)). Neuotrophins, such as brain-derived neurotrophic factor (BDNF) and neurotrophin-3 (NT-3), have been reported to up-regulate neural differentiation. Cell adhesion molecules, such as neural cellular adhesion molecules (N-CAM), also affect cell proliferation and differentiation. For example, bFGF and either N-CAM or BDNF have been used to generate active neural networks from primary cultures of neural progenitors isolated from the rat hippocampus. Mistry, S. K., Keefer, E. W., Cunningham, B. A., Edelman, G. M., Crossin, K. L., "Cultured rat hippocampal neural progenitors generate spontaneously active neural networks." *PNAS.* 99, pp. 1621-1626, (2002).

Although regulation of neural progenitor cell differentiation oil MEAs has been studied, it has not been shown that a reliable, efficient and/or cost-effective source of neural progenitor cells can induce the formation of functional neural network on MEAs. Therefore there currently exists a need to develop an efficient and effective method for generating neural network microelectrode arrays in a manner that enables continuous cellular proliferation.

BRIEF SUMMARY OF THE INVENTION

In one aspect, the present invention relates to a method for generating functional neural networks on MEAs. The method involves disassociating neural progenitor cells from an embryo, propagating the neural progenitor cells, passaging the neural progenitor cells and seeding the passaged neural progenitor cells on MEAs to produce a functional neural network. The neural progenitor cells may be continuously passaged to propagate an endless supply of neural progenitor cells. This method is capable of producing neural networks having similar, or potentially better physiological properties and detection sensitivities for environmental toxins than those produced from primary progenitor cells. The MEAs made by the methods of the present invention may be used to detect a broad range of biological, chemical and/or environmental threats.

DETAILED DESCRIPTION OF THE INVENTION

The present invention is directed to a method for producing MEAs from neural cells. The method involves disassociating neural progenitor cells from an embryo, propagating the neural progenitor cells, passaging the neural progenitor cells and seeding the neural progenitor cells on MEAs to produce a functional neural network. The resultant MEAs may then be used to determine the presence of biological, chemical or environmental threats by detecting electrophysiologic activity of the neural network in response to exposure to such threats.

It is possible to use standard or accepted controlled extraction methods to select a specific type of neural progenitor cell. Selected neural progenitor cells, which may include any neural progenitor cells, are first disassociated from an embryo. The embryonic progenitor cells may be any progenitor cells, selected from any region of any embryo and designated to form any neural tissue, originating from an embryo that has reached a desired or sufficient point of development. In certain embodiments, the selected neural progenitor cells are cortical progenitor cells. In another embodiment, the cells are mammalian cortical progenitor cells such as human, rat or mouse cells. In a specific embodiment, the selected progenitor cells are cortical progenitor cells isolated from a rat embryo on the 13$^{th}$ day of embryonic development, wherein the 1$^{st}$ day of embryonic development is defined as the day of conception. The process may involve any standard or accepted method for disassociation of the progenitor cells such as via mechanical titration. In one embodiment, the selected neural progenitor cells may be mixed with a small percentage of neural stem cells. In another embodiment, only neural progenitor cells are selected and cultured.

The disassociated neural progenitor cells may then be collected and propagated using any standard or accepted method, such as centrifugation and suspension in a serum-free medium. The serum-free medium is formulated to promote cellular propagation and to support the long-term survival of embryonic neurons and neuroglia and may contain neurotrophins and growth factors. Preferably, the serum-free medium comprises a neurobasal medium (NB) and at least one growth factor such as basic fibroblast growth factor (bFGF). Most preferably, the serum-free medium comprises NB, bFGF, epidermal growth factor (EGF), leukemia inhibitory factor (LIF) or a combination thereof.

The propagated neural progenitor cells are then passaged, which involves growing the neural progenitor cells in culture media that contain sufficient nutrients and components for inducing and regulating cellular growth. In a preferred embodiment, the culture media comprises neurobasal medium (NB) supplemented with B27 and about 0.5 mM L-glutamine on surfaces coated with fibronectin. More preferably, the culture media comprises fibronectin and poly-D-lysine (PDL). The neural progenitor cells are allowed to grow for a period of about 3-10 days, 3-7 days, 3-5 days, or, alternatively, 5-7 days. The resultant progenitor cells are then incubated in trypsin-ethylenediamine tetraacetic acid (EDTA). An effective amount of trypsin inhibitor is then added to the mixture of trypsin-EDTA. The mixture is then immediately centrifuged, and the supernatant is removed before the progenitor cells are resuspended in the serum-free medium. In a preferred embodiment, the trypsin-EDTA is incubated for about 5 minutes to about 10 minutes at about room temperature or 37° C. A trypsin inhibitor is then added in an amount of about 1/10 of the EDTA-trypsin mixture and immediately centrifuged at room temperature or about 4° C. before the progenitor cells are resuspended in the serum-free medium.

Upon completion of this first passaging step, the passaging step may be repeated one or more times to further propagate the neural progenitor cells by transferring the progenitor cells onto new culture media. Preferably the progenitor cells are passaged twice; more preferably the progenitor cells are passaged at least three times. Since large numbers of neural progenitor cells can be generated through cellular passaging, this process can provide a renewable source for neural network MEAs. Passaging enables the production of at least about 10 fold more progenitor cells after one passaging step, than that of non-passaged progenitor cells and can produce more than about 100 fold additional cells if three or more passaging steps are employed.

In one embodiment, to enhance passaging efficiency, a limited number of progenitor cells may be cultured during the first passaging step and in subsequent passaging steps, substantially more progenitor cells are cultured. In another embodiment, about twice the number of progenitor cells are plated for culturing during the second passaging step than during the first passaging step.

Upon resuspension of the neural progenitor cells in the serum-free medium, the cells may be counted and seeded onto the surface of the MEAs, with an amount of about 30,000 progenitor cells per MEA. The surfaces of the MEAs may be pretreated with PDL; and, optionally, the surfaces are pretreated with PDL and a cell adhesion molecule, such as fibronectin.

After seeding, the neural progenitor cells produce a neural network comprising a mixed culture of neurons and neuroglia, which may be maintained in the serum-free medium. In comparison to pure neural cultures, such mixed cultures are advantageous since neuroglia and neuroglia-conditioned saline are known to promote neural survival, differentiation and physiological maturation (Liu, Q. Y., Schaffner, A. E., Chang, Y. H., Barker, J. L., "Astrocyte-conditioned saline supports embryonic rat hippocampal neuron differentiation in short-term cultures," *J Neuroscience Methods* 86, pp. 71-7, (1998)). Consistent action potential activity resulting from such co-cultures suggests that neuronal-neuroglial co-cultures have a lifespan of about 6 to about 9 months.

Optionally, while the neural network is maintained in the serum-free medium, at least one compound may be added to promote and up-regulate cellular differentiation. In a preferred embodiment, the compound is a cellular growth factor, more preferably a neurotrophin, and most preferably a brain-derived neurotrophic factor (BDNF).

The resultant neural network MEAs may also be loaded into stainless steel recording chambers and stored in an incubator until ready for use. It is envisioned that the method of the present invention would be amenable to constructing various different portable cell-based biosensors 1, shown in FIG. 1, which are capable of detecting various environmental toxins by measuring the rate of change in action potential 2 across the neural network 5 from the reference electrode 3 to the microelectrode array electrode(s) 7 having the neural network 5 thereon, using a differential amplifier 4. Any suitable, conventional equipment may be employed to obtain and analyze information from differential amplifier 4, such as a computer connected for data acquisition from differential amplifier 4.

Figure 1:
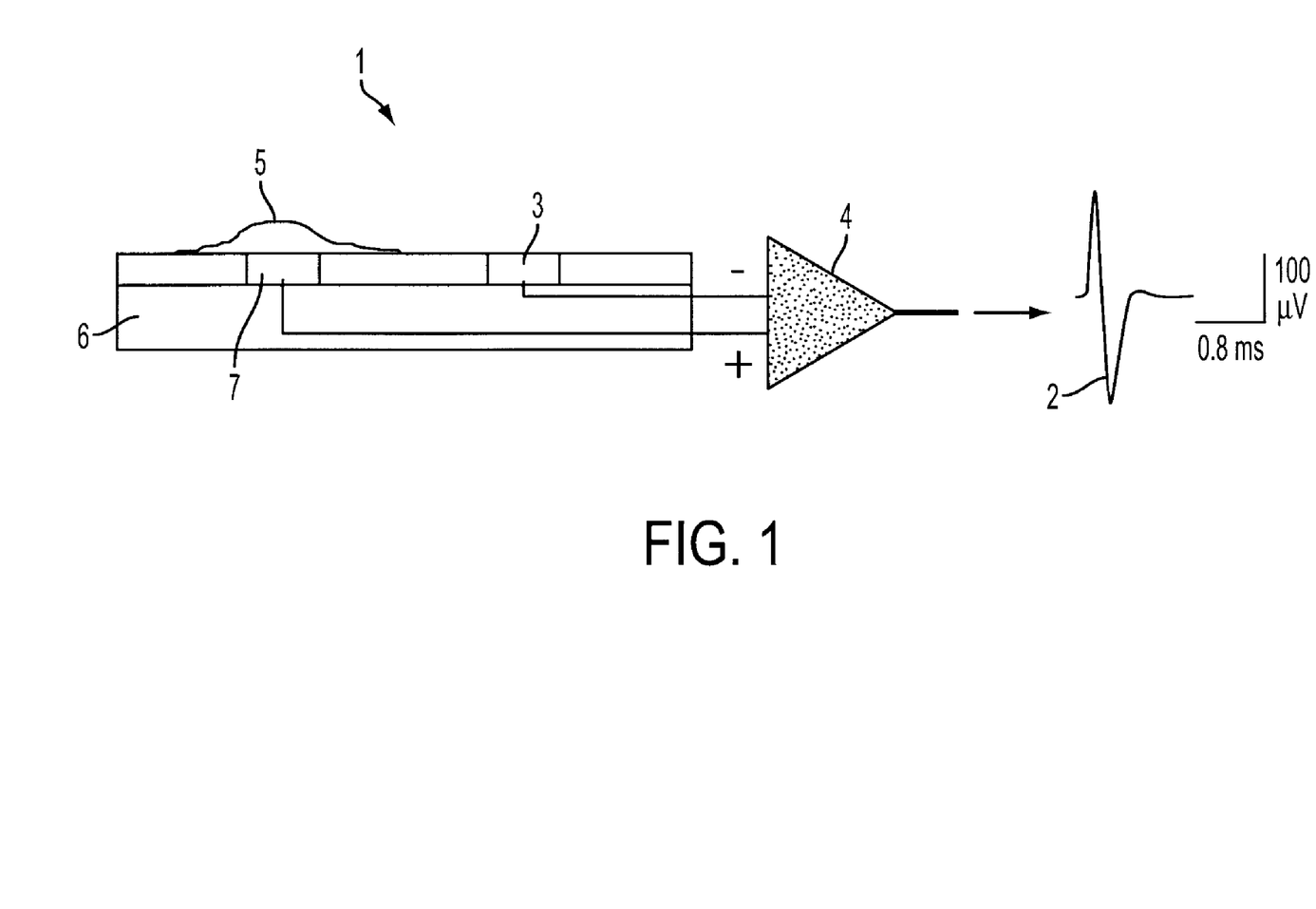
FIG. 1 is a schematic diagram of neural progenitor cell-derived neural networks on an MEA generating action potentials across the neural network.

Action potential activity recorded from the neural networks 5 on MEAs may be quantified using mean spike rate and, optionally, at least one burst parameter, such as burst rate, burst duration and number of spikes per burst. For example, action potential spikes may be detected using a threshold crossing algorithm with an adaptive threshold. In one embodiment, the minimum possible threshold may be selected to be about 25 µV, and the minimum time above the threshold may be selected to be about 100 µs.

FIG. 1 shows a schematic diagram of progenitor cell-derived neural networks 5 located on portable MEA 6 to generate action potential 2 across neural network 5. In one embodiment, the MEA may include transparent patterns of indium-tin oxide conductors as an electrode 7, about 10 µm wide, which are photoetched and passivated with a polyimide resin. Laser de-insulation of the resin may be used to produce at least 64 contact or recording sites 3 over an area of about 1 mm². The body or substrate 6 of the portable MEA may be constructed from any material, typically glass. Neural progenitor cell-derived neural networks function as the sensing elements of the biosensor 1.

The biosensor 1 may be used to quantify and/or detect the presence of various biological, chemical or environmental threats. Specifically, the array may be used to detect and quantify cellular reactions to various compounds including toxins, such as tetrodotoxin (TTX), botulinum toxin A, botulinum toxin B, tetanus toxin, algal toxins, such as domoic acid, saxitoxins (STX), brevetoxins, or other neurotoxins: nerve agents, such as bicuculline, DL-2-amino-5-phosphonovaleric acid (APV), 6-cyano-7-nitroquinoxaline-2,3-dione (CNQX), cadmium chloride ($CdCl_2$), methyl phosphonate, pinacolyl methylphosphonate, isopropyl methylphosphonate or other neurotransmitter antagonists and neurotransmitter inhibitors; bacterial agents: choking agents, such as tichloroisocyanuric acid or sodium hypochloride: fuel and/or combustion products, such as TMPP, JP-5, JP-8 or toluene; toxic metals, such as lead, mercury or trimethyl tin chloride; herbicides and/or pesticides, such as chloropyrifos: bioregulators, such as acetylcholine, ammonia, AMPA, apamin, APV, ascorbic acid, atropine, bicuculline, $Ca^{+2}$, carbachol, carbenoxolone, charybdotoxin, curare, cyclothiazide, diltiazem, Evan's Blue, GABA, glutamate, glutathione, glycine, L-733, 060, MCPG, $Mg^{+2}$, NBQX, NMDA, Norepinephrine, pralidoxime, $K^+$, SCH 50911, strychnine, verapamil or ZD7288: psychogenic and/or hallucinatory drugs, such as anandamide, chloroquine, ethanol, chlorpromazine, fluoxetine, prozac, haloperidol, methanandamide, methysergide, quinine or risperidone: n-acyl ethanolamines, such as palmitoyl, oleoyl, linoleyl, linolenyl, linolenyl, arachdonyl, CB1 agonists or CB1 antagonists: or miscellaneous compounds, such as propidium iodide, dimethyl sulfoxide, or anti-epileptic compounds.

The method of the present invention may be applicable for constructing various animal or human progenitor cell-based biosensors. Human embryonic stem cell lines can be used to form human neural stem cells and neural networks comprising neurons and neuroglia. It is envisioned that human cell-based biosensors may be more adept at detecting threats to humans. Additionally, this method could be used to generate a reproducible in vitro system for drug screening or could be used to screen pharmaceutical compounds for neuroactive effects.

The present invention advances the development of cell-based biosensors in that: the passaged neural progenitor cells may be used as a renewable source for generating an unlimited supply of neural networks, thereby reducing or eliminating dependence on animals, and the passaged neural progenitor derived networks have similar, if not better, physiological properties and/or detection sensitivity in comparison to non-passaged neuron-derived networks.

Example 1 and Comparative Example A

Two types of neural network MEAs were studied, one derived from primary neural stem and progenitor cells and the other derived from passaged primary neural stem and progenitor cells.

Neural network MEAs derived from primary neural stem cells and progenitor cells were produced by dissociation and expansion of cortical progenitor cells from rat embryos that were removed from their dams on the 13$^{th}$ day of embryonic development and placed into Earle's Balanced Salt Solution (EBSS). For reference purposes, the 1$^{st}$ day of embryonic development is defined as the day of conception established by the presence of a vaginal plug. The crown-rump length was measured to confirm the embryonic age. The cortical neuroepithelium was then dissected from the embryo. The areas dissected corresponded to the formative dorsal telencephalon, according to the atlas of the prenatal rat brain Altman, J. and Bayer, S. A., "Atlas of Prenatal Rat Brain Development," CRC Press, Inc., (1995). The embryonic tissue was dissociated by mechanical titration in EBSS with a sterile, fire-polished glass Pasteur pipette.

The cells were then collected by centrifugation and resuspended in a serum-free medium consisting of neurobasal medium (NB) supplemented with B27 and about 0.5 mM L-glutamine, and containing 30 ng/ml of recombinant human basic FGF (Intergen, Purchase, N.Y.). NB/B27 was used because it has been previously demonstrated to support the long-term survival of embryonic central neurons and tumor cell lines of neural origin.

A small portion of cells were taken out and then counted by trypan blue exclusion to measure the number of total viable cell, 30,000 neural stem cells and progenitor cells in bFGF-containing NB/B27 medium were then plated on the surfaces of MEAs that were pre-treated with poly-D-lysine (PDL) and fibronectin.

In this experiment, the MEA was a glass slide with electrodes located on its surface (see Pancrazio, J. J., Gray, S. A., Shubin, Y. S., Kulagina, N., Cuttino, D. S., Shaffer, K. S., Eisemann, K., Curran, A., Zim, B., Gross, G. W., and O'Shaughnessy, T. J., "A Portable Microelectrode Array Recording System Incorporating Cultured Neuronal Networks for Neurotoxin Detection," *Biosens. Bioelectron.* 18, p. 1339, (2003)). After seeding, cultured networks were constantly maintained at 37° C. in NB medium containing bFGF and supplemented with B27 for 5 days. The medium was then replaced with new NB/NB27 medium containing both bFGF and BDNF for 5 days. After this, the medium was then replaced with NB/B27 containing no growth factors, i.e. no bFGF or BDNF, for a period of three weeks. During this time, the medium was changed every five days. The resultant MEA neural network was loaded into stainless steel recording chambers having a volume of approximately 5 ml. The neural networks were then stored in a 10% $CO_2$ incubator until ready for use.

The neural network MEAs derived from passaged primary neural stem cells and progenitor cells were produced by dissociation and expansion of cortical progenitor cells from rat embryos that were also removed from their dams on the 13$^{th}$ day of embryonic development and placed into Earle's Balanced Salt solution. The embryonic tissue was dissociated by mechanical trituration in EBSS with a sterile, fire-polished glass Pasteur pipette.

The cells were then collected by centrifugation and resuspended in a serum-free medium consisting of neurobasal medium NB supplemented with B27 and about 0.5 mM L-glutamine, and containing 30 ng/ml of recombinant human bFGF (Intergen, Purchase, N.Y.).

The neural stem cells and progenitor cells were then passaged. After growing for about 7 days in 35 mm plastic dishes coated with PDL and fibronectin, the neural stem cells and progenitor cells were incubated in about 2 ml trypsin-ethylenediamine tetraacetic acid (EDTA) (0.5% w/v trypsin, 5.3 mM EDTA: Gibco, Gaithersburg, Md., USA) for about 10 min at about 37° C. About 0.2 ml trypsin inhibitor (Gibco BRL, Gaithersburg, Md., USA) was then added and the cells were centrifuged for 10 min at 1000×g. After centrifugation, the cells were resuspended in about 2 ml of NB/B27 containing about 0.5 mM L-glutamine and about 30 ng/ml bFGF. A small amount of cells were taken out and then counted by trypan blue exclusion to determine the total viable cell number.

The stem cells and progenitor cells were passaged a total of 3 times, about every 7 days using the method of Shaffer, K. M., Lin, H. J., Maric, D., Pancrazio, J., Stenger, D. A., Barker, J. L., Ma, W., "The use of $GABA_A$ receptors expressed in neural precursor cells for cell-based assays." *Biosensors & Bioelectronics*, 16, pp. 481-489, (2001).

After viable cells were counted by trypan blue exclusion, 30,000 neural stem cells and progenitor cells in bFGF-containing NB/B27 medium were then plated on the surfaces of MEAs that were pre-treated with PDL and fibronectin. Some of the neural stem cells and progenitor cells were plated on MEAs coated with PDL and laminin as controls. In this experiment, the MEA was a glass slide with electrodes located on its surface (see Pancrazio, J. J., Gray, S. A., Shubin, Y. S., Kulagina, N., Cuttino, D. S., Shaffer, K. S., Eisemann, K., Curran, A., Zim, B., Gross, G. W., and O'Shaughnessy, T. J., "A Portable Microelectrode Array Recording System Incorporating Cultured Neuronal Networks for Neurotoxin Detection," *Biosens. Bioelectron.* 18, p. 1339, (2003)). After seeding, cultured networks were maintained at 37° C. in NB medium containing bFGF and supplemented with B27 for 5 days. The medium was then replaced with new NB/NB27 medium containing both bFGF and BDNF for 5 days. After this, the medium was then replaced with NB/B27 containing no growth factors, i.e. no bFGF or BDNF, for a period of three weeks. During this time, the medium was changed every five days. The resultant MEA neural network was loaded into stainless steel recording chambers having a volume of approximately 5 ml. The neural networks were then stored in a 10% $CO_2$ incubator until ready for use.

Both the primary neural stem cells and progenitor cells and passaged neural stem cells and progenitor cells yielded a mixed culture of neurons and neuroglia. The passaged neural stem cells and progenitor cells produced 10 fold more cells than that of the non-passaged cells in the first passage and more than 100 fold more cells than that of the non-passaged cells by the third passage.

Immunocytochemistry was used to evaluate possible differentiation of progenitor cells along neural and neuroglial lineages. Cells were incubated with mouse monoclonal antibody MAP2 (a marker for neural lineage, 1:500, Sigma) and rabbit polyclonal anti-glial fibrillary acidic protein (GFAP, a marker for astrocyte, 1:500, Chemicon), followed by an incubation with rhodamine-conjugated donkey anti-mouse IgG and FITC-conjugated anti-rabbit IgG (Jackson Immunological Research, West Grove, Pa.), respectively. Immunostained cultures were examined with a Nikon Eclipse epifluorescence microscope.

Electrophysiologic measurements were then performed using the portable microelectrode array recording system developed at the Naval Research Laboratory (Gray, S. A., et al. "Design and demonstration of an automated cell-based biosensor," *Biosensors & Bioelectron.*, 16, pp. 535-542, (2001): Pancrazio, J. J., Gray, S. A., Shubin, Y. S., Kulagina, N., Cuttino, D. S., Shaffer, K. S., Eisemann, K., Curran, A., Zim, B., Gross, G. W., and O'Shaughnessy, T. J., "A Portable Microelectrode Array Recording System Incorporating Cultured Neuronal Networks for Neurotoxin Detection." *Biosens. Bioelectron.* 18, p. 1339, (2003)). The portable biosensor included an aluminum case containing pumps, valves, and temperature controllers with amplifiers and filters capable of processing microvolt-level extracellular signals and a high-level user interface for real-time monitoring of neural network activity. The system integrates temperature and fluidics control with on-line monitoring and recording of neural extracellular potentials derived from MEAs. Extracellular recordings were performed in a solution consisting of Minimum Essential Medium (MEM) supplemented with about 25 mM glucose, about 40 mM N-[2-hydroxyethyl]-piperazine-N-[2-ethanesulfonic acid] (HEPES), and about 26 mM $NaHCO_3$ at a maintained pH of 7.4 in standard atmosphere. Networks were then perfused with a flow rate of about 1 ml/min in a recirculation bath with a reservoir such that the total media volume was about 40 ml. The cell recording chamber temperature was maintained within a range of about 37±0.1° C. The control medium perfusion continued for about 30-40 minutes in order to establish a stable baseline of electrophysiological parameters of a network.

Action potential activity recorded from the neural networks cultured on MEAs were quantified using mean spike rate and several burst parameters, including burst rate, burst duration and number of spikes per burst. The data was sampled at a rate of 40 kHz per channel. Spikes were detected using a threshold crossing algorithm with an adaptive threshold, wherein the minimum possible threshold was about 25 μV, and a minimum time above a threshold was about 100 μs. Mean spike rate was calculated in one minute intervals by first computing the spike rate per channel and then generating the mean spike rate across all active channels.

Example 2 and Comparative Example B

The physiological properties of primary cortical stem cell and progenitor cell cultures were compared to that of passaged cortical stem cell and progenitor cell cultures. The primary and passaged cortical stem cell and progenitor cell cultures were derived from a rat embryo that was removed from the dam on the 13$^{th}$ day of development and were made according to the methods disclosed in Example 1 and Comparative Example A, except that after the cultured networks were maintained at 37° C. in NB medium containing bFGF and supplemented with B27 for 5 days, about 100 ng/mL of BDNF was added to the medium, and the cells in the BDNF composition were allowed to incubate for another 5 days.

Figure 2A:
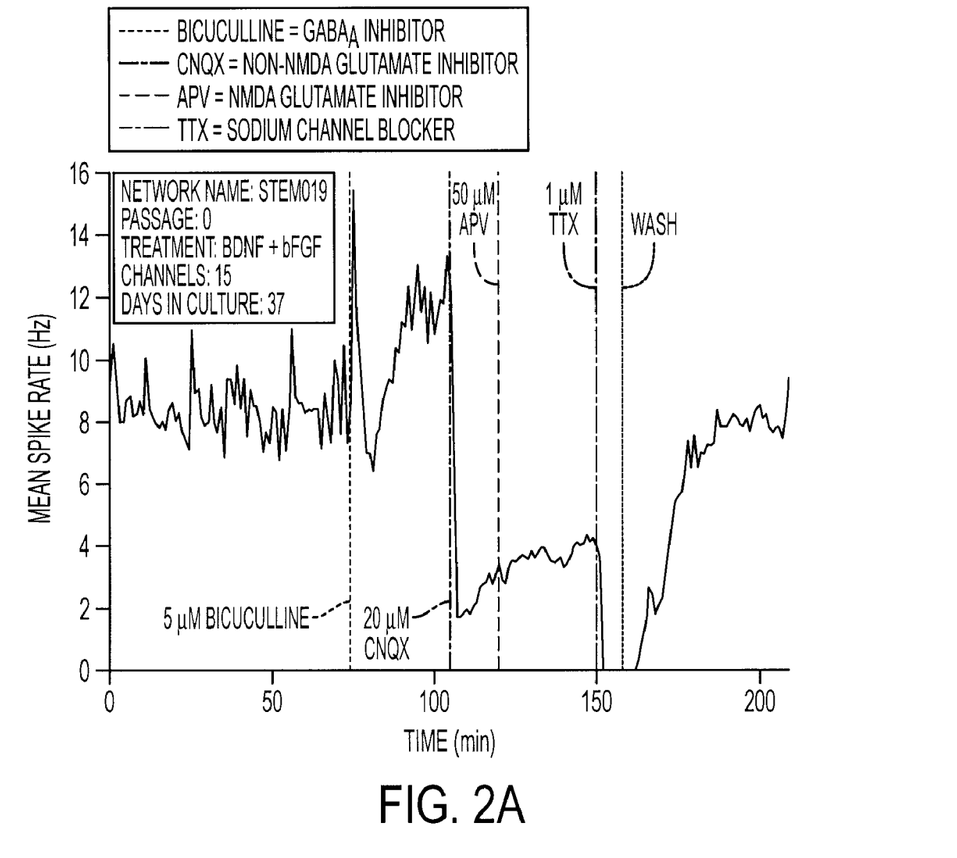
FIG. 2(a) is a graph of mean action potential spike rate as a function of time for a 37 day old non-passaged cortical progenitor cell culture treated with BDNF and bFGF.

Primary cortical stem cell and progenitor cell cultures that have been cultured for one month on a MEA differentiated into neurons, stained red by anti-MAP-2 antibodies, and neuroglia, stained green by anti-GFAP antibodies. FIG. 2(*a*) shows the mean action potential spike rate as a function of time for 37 day old primary cortical stem cell and progenitor cell cultures treated with BDNF and bFGF. The cortical stem cell and progenitor cell cultures were seeded on a protable MEA and placed into a stainless steel recording chamber. A recirculating flow of HEPES-MEM media having a total volume of about 40 ml was initiated, while culture temperature was maintained at about 37±0.1° C. After assessing the activity across 64 electrodes on the microelectrode array, the strongest 15 were chosen for high frequency recordings. The mean spike rate (MSR) for these 15 channels, which was calculated once per minute for the duration of the experiment, is shown in FIG. 2(*a*).

At the times indicated in FIG. 2(*a*), a series of neurotoxins, namely bicuculline, CNQX, APV and tetrodotoxin (TTX), were added to the recirculating bath. Once a toxin was added it remained present throughout the remainder of the experiment until the system was washed or perfused with fresh media across the neural network. As shown in FIG. 2(*a*), the network reacted to bicuculline, a $GABA_A$ inhibitor, with an increase in MSR and responded to the later introduction of CNQX, a non-NMDA glutamate inhibitor, with a decrease in MSR. No additional decrease in network activity was seen with the addition of APV. Upon the introduction of the final toxin, TTX, a sodium channel blocker, all activity in the network was eliminated. The subsequent wash reversed the total blockade of action potential spike activity. The responses to bicuculline and CNQX are typical of primary murine neural networks and indicate the presence of inhibitory $GABA_A$ and excitatory non-NMDA glutamate synapses. The failure of APV to evoke a response after CNQX was already present is also typical of primary networks. Blockade of the non-NMDA glutamate synapses is typically sufficient to eliminate all synaptically derived spikes in a network. The remaining activity is the result of the presence of intrinsic spike production within a small subpopulation of neurons. The total elimination of spike activity by TTX, a sodium channel blocker, demonstrates that all spike behavior present in the network was due to sodium derived action potentials. The actions of all four applied drugs were found to be reversible by the wash step.

Figure 2B:
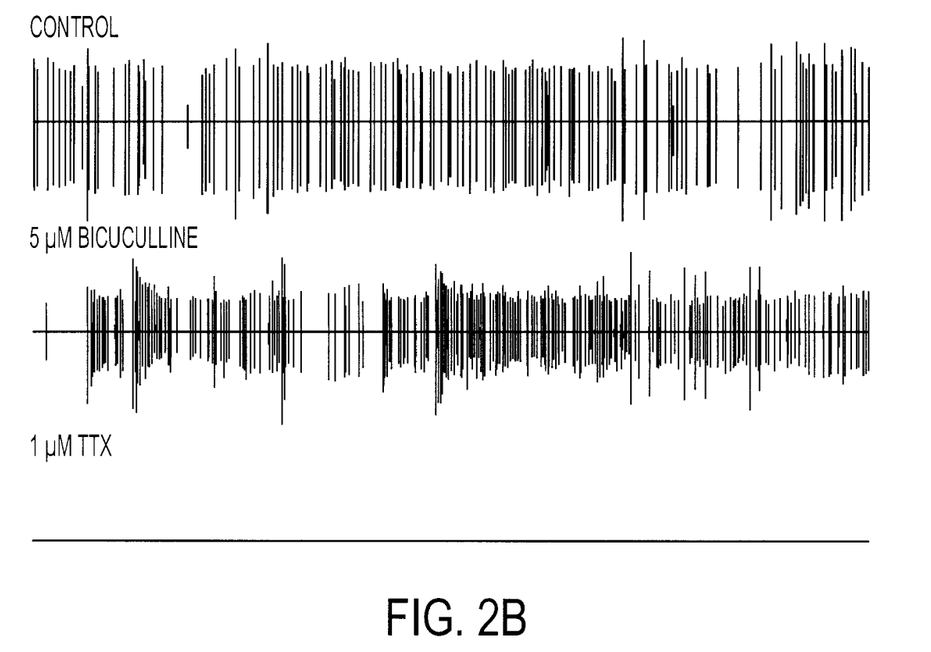
FIG. 2(b) shows three sets of 10 second traces of raw action potential spike activity from a single channel of the neural network of FIG. 2(a) in a control state, in which no neurotoxin has been added, in a bicuculline experimental state, in which bicuculline has been added and in a TTX experimental state, in which TTX has been added.

FIG. 2(*b*) show three sets of 10 second traces of raw action potential spike activity from a single channel of the neural network of FIG. 2(*a*) in a control state, in which no neurotoxin has been added, in a bicuculline experimental state, in which bicuculline has been added and in a TTX experimental state, in which TTX has been added. The bicuculline trace shows the increased activity and change in burst pattern associated with the block of $GABA_A$ receptors. The final trace was taken from the region after TTX was introduced, at which time the other 3 toxins, bicuculline, APV and CNQX, are also present.

Figure 3A:
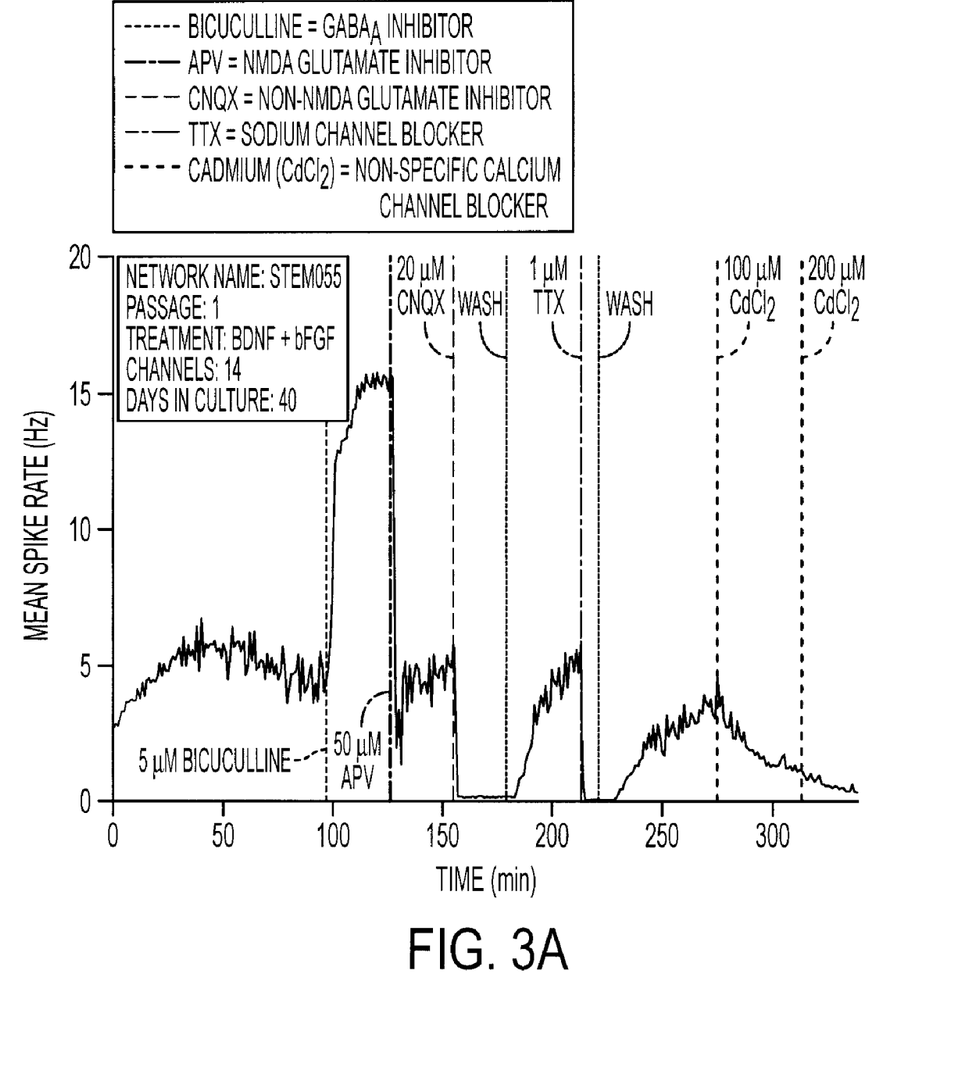
FIG. 3(a) is a graph of mean action potential spike rate as a function of time for a 40 day old one time passaged cortical progenitor cell culture treated with BDNF and bFGF.
Figure 3B:
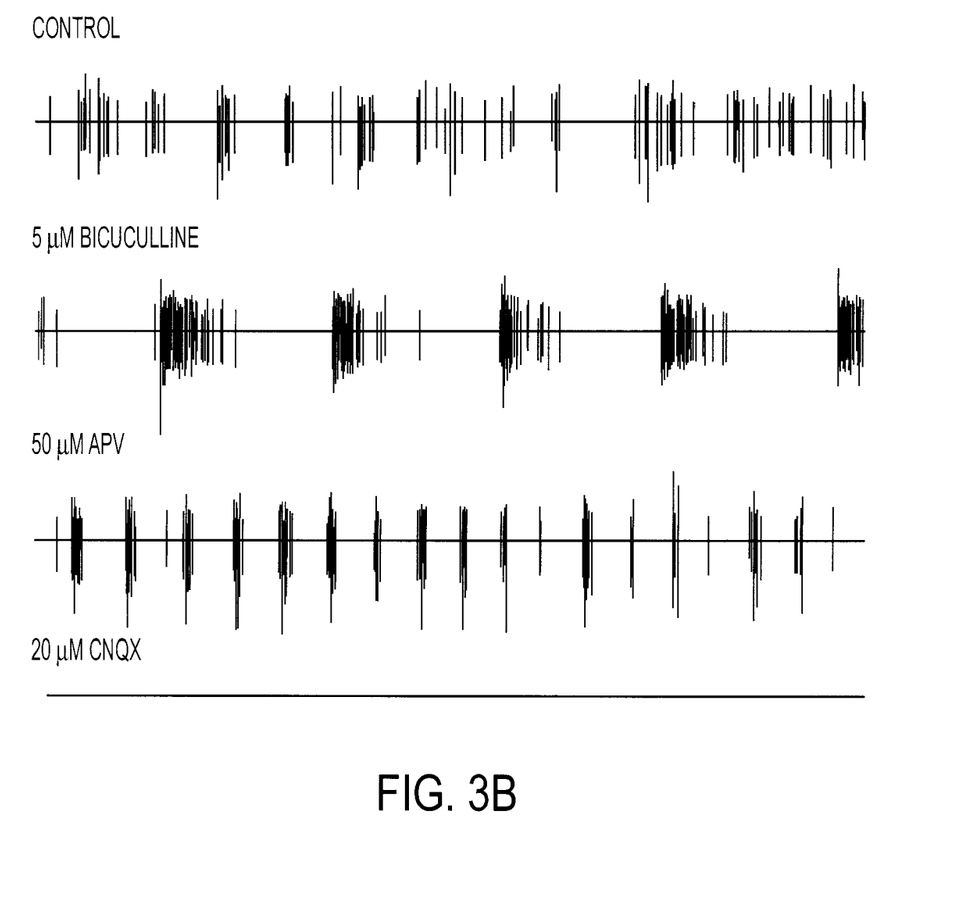
FIG. 3(b) shows four sets of 10 second traces of raw action potential spike activity from a single channel of the neural network of FIG. 3(a) in a control state, in which no neurotoxin has been added, in a bicuculline experimental state, in which bicuculline has been added, in a APV experimental state, in which APV has been added and in a CNQX experimental state, in which CNQX has been added.

By comparison, FIGS. 3(*a*)-3(*b*) show the pharmacological properties of passaged cortical stem and progenitor cell derived neural networks. The cortical stem cells and progenitor cells were derived from a rat embryo taken from a dam on the 13$^{th}$ day of development. Passaged primary cortical stem cell and progenitor cell cultures that have been cultured for a period of one month on a MEA differentiated into neurons, stained red by anti-MAP-2 antibodies, and neuroglia, stained green by anti-GFAP antibodies.

FIG. 3(a) shows the mean action potential spike rate as a function of time for 40 day old cortical stem cell and progenitor cell cultures that were passaged one time and treated with BDNF and bFGF. The neural stem cell and progenitor cell cultures were seeded on a portable MEA and placed into a stainless steel recording chamber. A recirculating flow of HEPES-MEM media having a total volume of about 40 ml was initiated, while culture temperature was maintained at about 37±0.1° C. After assessing the activity across 64 electrodes on the MEA, the strongest 14 were chosen for high frequency recordings. The mean spike rate (MSR) for these 14 channels, which was calculated once per minute for the duration of the experiment, is shown in FIG. 3(a). At the times indicated in FIG. 3(a), a series of neurotoxins, namely bicuculline, CNQX, APV, TTX and cadmium chloride, were added to the recirculating bath. Once a toxin was added it remained present throughout the remainder of the experiment until the system was washed or perfused with fresh media across the neural network. As shown in FIG. 3(a), the network reacted to bicuculline with an increase in MSR, and responded to the later introduction of APV with a decrease in MSR. When CNQX was then added, a further decrease in activity was noted, TTX was demonstrated to eliminate all activity in the network, which effect was subsequently reversed by a washing step. Finally, the neural network was also found to be responsive to the presence of the heavy metal cadmium, a known non-specific calcium channel inhibitor at low concentrations.

In comparison to the activity of the primary cortical stem cell and progenitor cell derived neural networks, the passaged cortical stem cell and progenitor cell derived neural networks demonstrated similar responses to bicuculline and CNQX. By adding APV prior to CNQX a decrease in spike rate was found, indicative of the presence of excitatory NMDA glutamate synapses. This is consistent with primary murine neural networks where APV blocks only a fraction of synaptic activity. A small amount of intrinsic spike production remained after CNQX was added, but this was eliminated by the introduction of TTX. The actions of the four toxins were reversed by washing and the network was further found to be responsive to the heavy metal cadmium, which is a known calcium channel inhibitor at low concentrations and is cytotoxic at higher concentrations.

FIG. 3(b) shows four sets of 10 second traces of raw action potential spike activity from a single channel of the neural network of FIG. 3(a) in a control state, in which no neurotoxin has been added, in a bicuculline experimental state, in which bicuculline has been added, in an APV experimental state, in which APV has been added, and in a CNQX experimental state, in which CNQX has been added. The bicuculline trace shows increased activity and a change in burst pattern associated with the block of $GABA_A$ receptors. The APV trace shows the incremental effects of APV on both spike rate and burst pattern, while the final trace shows a near total blockade of action potentials by CNQX.

Example 3

Neuroepithelial stem cells and progenitor cells were isolated from embryonic day 13 rat cortex and subsequently expanded, passaged and differentiated into neurons and neuroglia over MEAs. Passaged neuroepithelial cells stem cells and progenitor cells were expanded for 5 days after passaging and seeding on MEAs. Passaged stem cells and progenitor cells that were grown on a MEA for a period of 2 months, differentiated into neurons, stained red by anti-MAP-2 antibodies, and neuroglia, stained green by anti-GFAP antibodies.

Example 4

The effects of bFGF and a composition of bFGF and BDNF on unpassaged primary neural stem and progenitor cell differentiation were investigated. The cortical stem cells and progenitor cells were derived from a rat embryo taken from a dam on the $13^{th}$ day of development. The neurons were stained red by anti-MAP2 antibodies, and the neuroglia were stained green by anti-GFAP antibodies. GFAP+ stained neuroglia were well developed under both conditions, but the bFGF and BDNF treatments produced more neurons and appeared to provide the most promising set of conditions for neural network generation. Additionally, treatment with bFGF and BDNF produces a longer neurite process and better neurite outgrowth in the neurons, which can promote functional neural network activity.

Having described the preferred embodiments of the invention which are intended to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, the intended scope of protection is set forth in the appended claims.

What is claimed as new and desired to be protected by Letters Patent of the United States is:

1. A method for making a neural network microelectrode array comprising the steps of:
   dissociating select neural progenitor cells from an embryo;
   propagating said dissociated neural progenitor cells in media comprising bFGF;
   passaging the propagated neural progenitor cells;
   seeding said passaged neural progenitor cells on a microelectrode array and cultivating said passaged neural progenitor cells in media comprising BDNF to produce a functional neural network; and
   assembling a neural network microelectrode array biosensor employing the functional neural network obtained in said seeding step.

2. The method of claim 1 wherein said select neural progenitor cells are cortical progenitor cells.

3. The method of claim 1 wherein said progenitor cells are obtained from a mammal.

4. The method of claim 1 wherein said progenitor cells are obtained from one or more of a human, a mouse or a rat.

5. The method of claim 1 wherein said passaging step comprises the step of culturing said neural progenitor cells for a growth period in a culture media comprising poly-D-lysine and fibronectin.

6. The method of claim 5 wherein said growth period is from about 3 days to about 10 days.

7. The method of claim 5 wherein said growth period is from about 3 days to about 5 days.

8. The method of claim 5 wherein said growth period is from about 5 days to about 7 days.

9. The method of claim 5 wherein said passaging step comprises the steps of centrifuging said neural progenitor cells following said growth period and subsequently suspending said neural progenitor cells in a serum-free medium.

10. The method of claim 9 wherein said serum-free medium comprises at least one material selected from the group consisting of: a growth factor, a neurobasal medium and combinations thereof.

11. The method of claim 10 wherein said growth factor comprises basic fibroblast growth factor.

12. The method of claim 1 wherein in said seeding step said media is serum-free medium and wherein said serum-free medium comprises at least one neurotrophin.

13. The method of claim 1 wherein in said passaging step said neural progenitor cells are passaged at least twice for 3-10 days in culture media.

14. The method of claim 1, wherein said passaging results in an increase number of cells by ten-fold or more.

15. The method of claim 1, wherein said media comprising BDNF further comprises bFGF.

16. A method for making a neural network microelectrode array comprising the steps of:

dissociating select neural progenitor cells from an embryo;

propagating said dissociated neural progenitor cells, thereby increasing their number by ten-fold or more;

passaging said propagated neural progenitor cells in a serum-free medium comprising bFGF;

seeding said passaged neural progenitor cells in a serum-free medium comprising bFGF and BDNF onto a microelectrode array to produce a functional neural network; and assembling a neural network microelectrode array biosensor comprising the neural network obtained in said seeding step.

* * * * *